United States Patent
Kamal et al.

(12) 
(10) Patent No.: US 11,447,688 B2
(45) Date of Patent: Sep. 20, 2022

(54) METHODS FOR CLAY SWELLING INHIBITION USING GEMINI SURFACTANTS CONTAINING A SATURATED LINKER

(71) Applicant: KING FAHD UNIVERSITY OF PETROLEUM AND MINERALS, Dhahran (SA)

(72) Inventors: Muhammad Shahzad Kamal, Dhahran (SA); S.M. Shakil Hussain, Dhahran (SA); Mobeen Murtaza, Dhahran (SA); Mohamed Mahmoud, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 16/777,221

(22) Filed: Jan. 30, 2020

(65) Prior Publication Data
US 2021/0238472 A1    Aug. 5, 2021

(51) Int. Cl.
*C09K 8/86* (2006.01)
*C09K 8/60* (2006.01)
*C07C 235/10* (2006.01)

(52) U.S. Cl.
CPC ............ *C09K 8/607* (2013.01); *C07C 235/10* (2013.01); *C09K 8/602* (2013.01); *C09K 8/86* (2013.01)

(58) Field of Classification Search
CPC .......... C09K 8/607; C09K 8/602; C09K 8/86; C09K 8/575; C09K 2208/12
See application file for complete search history.

(56) References Cited

U.S. PATENT DOCUMENTS

| | | | |
|---|---|---|---|
| 2,855,290 A | 10/1958 | Freeman | |
| 2,991,290 A | 7/1961 | Shapiro et al. | |
| 3,766,267 A | 10/1973 | Zak et al. | |
| 3,855,290 A | 12/1974 | Zak et al. | |
| 4,312,813 A | 1/1982 | Lindemann et al. | |
| 2017/0081582 A1* | 3/2017 | Ghumare | C09K 8/74 |

OTHER PUBLICATIONS

Hussain (S.M.S. Hussain, et al, Effect of the number of ethylene oxide units on the properties of synthesized tailor-made cationic gemini surfactants for oilfield applications, Journal of Molecular Structure 1196 (2019) 851-860).*

Seymour L. Shapiro, et al., "Aminoalkylamides and Oxazolidinediones", Journal of the American Chemical Society, vol. 81, Jun. 20, 1959, pp. 3083-3088.

* cited by examiner

*Primary Examiner* — Kumar R Bhushan
(74) *Attorney, Agent, or Firm* — Oblon, McClelland, Maier & Neustadt, L.L.P.

(57) ABSTRACT

Methods of controlling clay swelling and stabilizing subterranean geological formations containing swellable clays (e.g., montmorillonite, bentonite) are described. The methods involve treating the swellable clays with a composition containing an amidoamine-based gemini surfactant. The gemini surfactant has dual chains connected via an alkylene linker, whereby each chain contains a quaternary ammonium head group and an ethoxylated alkyl tail. As examined by linear swelling and free swelling tests, use of the gemini surfactant is effective in reducing swelling of the clays.

16 Claims, 7 Drawing Sheets

METHODS FOR CLAY SWELLING INHIBITION USING GEMINI SURFACTANTS CONTAINING A SATURATED LINKER

BACKGROUND OF THE INVENTION

Technical Field

The present disclosure relates to methods of stabilizing a subterranean geological formation containing swellable clays using a gemini surfactant. The gemini surfactant has two chains connected by an alkylene linker, whereby each chain contains a quaternary ammonium head group, ethoxylate units, and an alkyl tail.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Drilling fluids are used in drilling operations to perform many functions including transportation of cuttings, lubrication, fluid loss control, and shale swelling inhibition. Drilling fluids are divided into two general types: oil-based drilling fluids and water-based drilling fluids. Oil-based drilling fluids have superior properties but are avoided due to stringent environmental regulations and high cost. Water-based drilling fluids are generally considered to be environmentally friendly. However, water-based drilling fluids can have a detrimental effect on the wellbore stability due to their interaction with the shale formation.

Clay swelling during drilling operations can create problems, such as bit balling, stuck pipes, disintegration of shale cuttings, and low hole-cleaning efficiency. In extreme cases, clay swelling results in damage of the drilling assembly, loss of circulation, and destruction of the complete well. These issues can complicate drilling operations and lead to significantly increased production and recovery costs. It has been estimated that issues relating to wellbore instability could increase the cost of oil drilling by 10%. For these reasons, there is a long felt need for shale swelling inhibitors that effectively control clay swelling without adversely affecting the performance of drilling fluids.

In view of the forgoing, one objective of the present disclosure is to provide a method of inhibiting clay swelling and stabilizing a subterranean geological formation containing swellable clays using a composition containing a gemini surfactant. The composition may further include an aqueous base fluid.

BRIEF SUMMARY OF THE INVENTION

An aspect of the present disclosure relates to a method of stabilizing a subterranean geological formation containing a swellable clay. The method involves treating the swellable clay with a composition comprising a surfactant of formula (I) or a solvate thereof, a tautomer thereof, a stereoisomer thereof, or a mixture thereof, wherein (i) each of $R_1$ and $R_2$ are independently selected from the group consisting of a hydrogen, an optionally substituted alkyl, an optionally substituted cycloalkyl, and an optionally substituted arylalkyl, (ii) each of $R_3$ and $R_4$ are independently selected from the group consisting of an optionally substituted alkyl, an optionally substituted cycloalkyl, and an optionally substituted arylalkyl, (iii) L is a $C_{7-16}$ alkylene linker, (iv) each of n is independently an integer in a range of 1-15, (v) each of x is independently an integer in a range of 5-21, (vi) each of y is independently an integer in a range of 2-5, and (vii) X is an anion selected from the group consisting of a halide ion, a hexafluorophosphate ion, a trifluoromethanesulfonate ion, and a tetrafluoroborate ion.

In one embodiment, the swellable clay is at least one selected from the group consisting of a smectite clay, a kaolin clay, an illite clay, a chlorite clay, and a sepiolite clay.

In one embodiment, the swellable clay is a smectite clay.

In a further embodiment, the smectite clay comprises montmorillonite.

In one embodiment, the composition further comprises an aqueous base fluid.

In one embodiment, the surfactant of formula (I) is present in an amount of 0.001-5 wt. % relative to a total weight of the composition.

In one embodiment, each of $R_1$ and $R_2$ are independently a hydrogen, or a methyl. In one embodiment, each of $R_1$ and $R_2$ are a hydrogen.

In one embodiment, each of $R_3$ and $R_4$ are independently selected from the group consisting of a methyl, an ethyl, and an isopropyl.

In one embodiment, each of $R_3$ and $R_4$ are a methyl.

In one embodiment, L is a linear $C_{8-12}$ alkylene.

In one embodiment, L is selected from the group consisting of $-(CH_2)_8-$, $-(CH_2)_{10}-$, and $-(CH_2)_{12}-$.

In one embodiment, L is $-(CH_2)_{12}-$.

In one embodiment, each of n is an integer in a range of 2-11.

In one embodiment, each of x is an integer in a range of 11-13.

In one embodiment, each of y is 3.

In one embodiment, X is bromide.

In one embodiment, the surfactant is selected from the group consisting of a surfactant represented by formula (II)

(I)

$$H_3C{\left(\right)}_x{\left[O\right]}_n O \overset{O}{\underset{}{\|}} \overset{R_1 \; R_2}{\underset{R_3 \; R_4}{N^+}} L \overset{R_1 \; R_2}{\underset{R_3 \; R_4}{N^+}} \overset{O}{\underset{}{\|}} O {\left[\right]}_n {\left(\right)}_x CH_3 \quad 2X^-$$

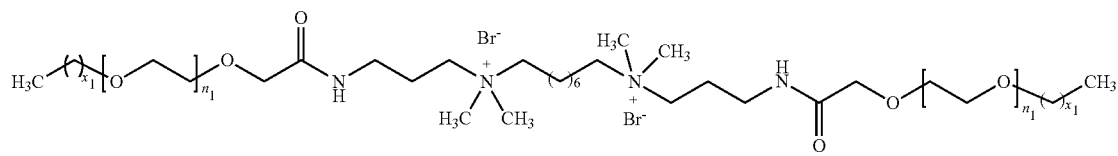

(II)

a surfactant represented by formula (III)

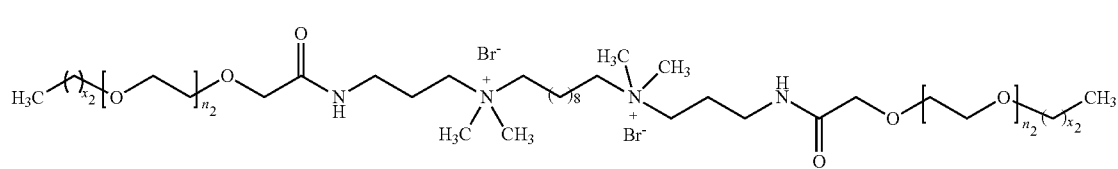

(III)

and
a surfactant represented by formula (IV)

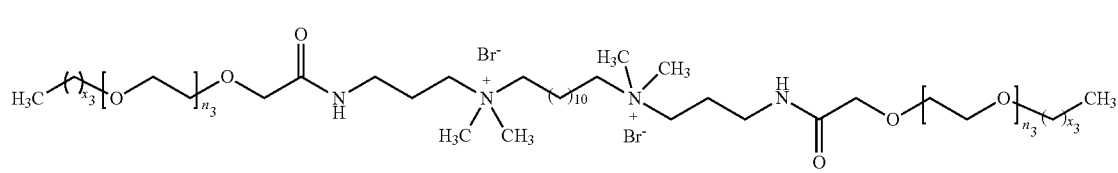

(IV)

wherein (i) each of $n_1$, $n_2$, and $n_3$ are independently an integer in a range of 2-11, and (ii) each of $x_1$, $x_2$, and $x_3$ are independently an integer in a range of 11-13.

In one embodiment, the surfactant is represented by formula (IV)

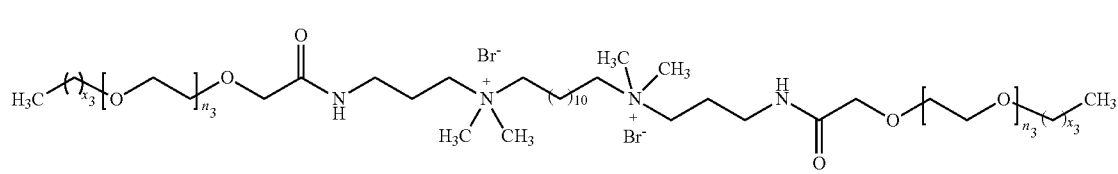

(IV)

wherein (i) each of $n_3$ is independently an integer in a range of 2-11, and (ii) each of $x_3$ is independently an integer in a range of 11-13.

In one embodiment, the composition is substantially free of a potassium salt.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
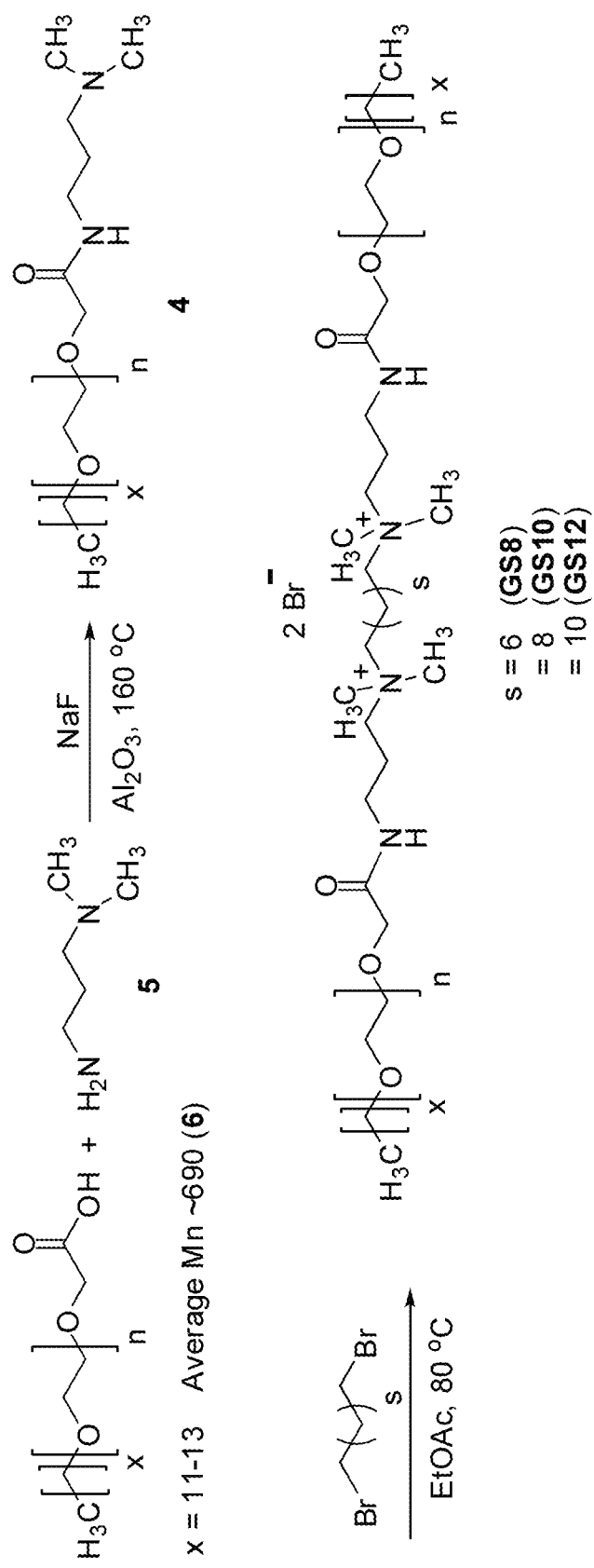
FIG. 1 is a synthesis scheme for the preparation of surfactants GS8, GS10, and GS12 from 1,8-dibromooctane, 1,10-dibromodecane, and 1,12-dibromododecane, respectively, as well as an amidation product of a carboxylic acid having a number average molecular weight of about 690 g/mol and 3-(dimethylamino)-1-propylamine.

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the word "about" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), or +/−15% of the stated value (or range of values).

When referencing compositions used herein, the phrase "substantially free", unless otherwise specified, describes an amount of a particular component present in the composition being less than about 1 wt. %, preferably less than about 0.5 wt. %, more preferably less than about 0.1 wt. %, even more preferably less than about 0.05 wt. %, yet even more preferably 0 wt. %, relative to a total weight of the composition.

As used herein, the terms "compound", "surfactant", and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images.

Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the ring systems, stereogenic centers, and the like can all be present in the compounds, and all such stable isomers are contemplated in the present disclosure. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —$SO_2NH_2$), substituted sulfonamide, nitro, cyano, carboxy, unsubstituted amide (i.e. —$CONH_2$), substituted amide (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those of ordinary skill in the art, for example, as taught in Greene, et al., "Protective Groups in Organic Synthesis", John Wiley and Sons, Second Edition, 1991, hereby incorporated by reference in its entirety.

As used herein, the term "alkyl" unless otherwise specified refers to both branched and straight-chain saturated aliphatic primary, secondary, and/or tertiary hydrocarbons having a specified number of carbon atoms. The term "alkylene" as used herein means a divalent counterpart of an alkyl group. For example, "$C_7$ to $C_{16}$ alkylene" or "$C_{7-16}$ alkylene" denotes a divalent alkyl chain having 7 to 16 carbon atoms. The alkyl or alkylene groups typically include $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, and $C_{16}$. Exemplary alkyls include, but are not limited to, methyl, trifluoromethyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, 2,3-dimethylbutyl, 2-ethylhexyl, n-heptyl, n-octyl, n-nonyl, 3,7-dimethyloctyl, n-decyl, n-undecyl, n-dodecyl, n-tridecyl, and 2-propylheptyl. Non-limiting examples of alkylene groups include, but are not limited to, —$CH_2CH_2$—, —$C(CH_3)_2CH_2$—, —$CH_2C(CH_3)_2CH_2$—, —$CH_2CH(CH_3)CH_2$—, —$CH_2CH(CH_2CH_2CH_2CH_3)$—, —$CH_2C(CH_3)_2CH(CH(CH_3)_2)$—, —$CH_2CH(CH_2CH_3)CH_2CH_2CH_2CH_2$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, and —$(CH_2)_{16}$—.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure. The term "cycloalkylene" as used herein means divalent counterpart of a cycloalkyl group.

The term "aryl", as used herein, and unless otherwise specified, refers to a substituent that is derived from an aromatic hydrocarbon (arene) that has had a hydrogen atom removed from a ring carbon atom. Aryl includes phenyl, biphenyl, naphthyl, anthracenyl, and the like.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "halide", as used herein, means fluoride, chloride, bromide, and iodide.

The term "halogen", as used herein, means fluoro, chloro, bromo and iodo.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, and isotopes of oxygen include $^{16}O$, $^{17}O$ and $^{18}O$. Isotopically labeled compounds of the disclosure can generally be prepared by conventional techniques known to those of ordinary skill in the art or by processes and methods analogous to those described herein, using an appropriate isotopically labeled reagent in place of the non-labeled reagent otherwise employed.

An aspect of the present disclosure relates to a method of stabilizing a subterranean geological formation containing a swellable clay using a composition including a surfactant of formula (I)

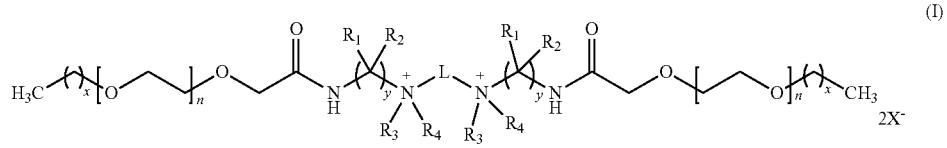

(I)

or a solvate thereof, a tautomer thereof, a stereoisomer thereof, or a mixture thereof. Gemini surfactants (or dimeric surfactants) have two hydrophilic groups and two hydrophobic groups in one molecule, in contrast to conventional surfactants that generally have a single hydrophilic group and a single hydrophobic group in one molecule. Gemini surfactants may be anionic, cationic, nonionic, or amphoteric. In one embodiment, the surfactant of formula (I) is a gemini surfactant.

Compared to their monomeric counterparts having one hydrophilic group and one hydrophobic group, gemini cationic surfactants containing ammonium headgroups exhibit superior physicochemical properties including lower critical micelle concentration (CMC), higher interface/surface properties, greater thermal stability and solubility, as well as better aggregation behavior and compatibility with carbonate rocks [Wang, Y.; Jiang, Y.; Geng, T.; Ju, H.; Duan, S. Synthesis, surface/interfacial properties, and biological activity of amide-based gemini cationic surfactants with hydroxyl in the spacer group. *Colloids and Surfaces A: Physicochemical and Engineering Aspects* 2019, 563, 1-10; Kaczerewska, O.; Brycki, B.; Ribosa, I.; Comelles, F.; Garcia, M. T. Cationic gemini surfactants containing an o-substituted spacer and hydroxyethyl moiety in the polar heads: Self-assembly, biodegradability and aquatic toxicity. *Journal of industrial and engineering chemistry* 2018, 59, 141-148; Lim, J.; Kang, E.; Lee, H.; Lee, B. Synthesis and interfacial properties of ethoxylated cationic surfactants derived from n-dodecyl glycidyl ether. *Journal of Industrial and Engineering Chemistry* 2015, 22, 75-82; and Bhat, I. A.; Roy, B. Synthesis and biophysical analysis of a novel gemini surfactant with lysozyme: Industrial perspective. *Journal of industrial and engineering chemistry* 2018, 63, 348-358, each incorporated herein by reference in their entirety]. In the past decades, these gemini cationic surfactants have been used extensively for oilfield applications including fracturing, micellar slugging, foam generation, reservoir stimulation, wettability modification, enhanced oil recovery, corrosion inhibition, and crude oil spills dispersion and collection [Zhou, M.; Zhang, Z.; Xu, D.; Hou, L.; Zhao, W.; Nie, X.; Zhou, L.; Zhao, J. Synthesis of three gemini betaine surfactants and their surface active properties. *Journal of the Taiwan Institute of Chemical Engineers* 2017, 74, 7-13; and Wang, Y.; Jiang, Y.; Geng, T.; Ju, H.; Duan, S. Synthesis, surface/interfacial properties, and biological activity of amide-based gemini cationic surfactants with hydroxyl in the spacer group. *Colloids and Surfaces A: Physicochemical and Engineering Aspects* 2019, 563, 1-10, each incorporated herein by reference in their entirety].

In formula (I) each of $R_1$ and $R_2$ are independently selected from the group consisting of a hydrogen, an optionally substituted alkyl, an optionally substituted cycloalkyl, and an optionally substituted arylalkyl. In one or more embodiments, each of $R_1$ and $R_2$ are independently a hydrogen, or a methyl. In one embodiment, each of $R_1$ and $R_2$ are the same. In another embodiment, each of $R_1$ and $R_2$ are different. In a preferred embodiment, each of $R_1$ and $R_2$ are a hydrogen.

Each of $R_3$ and $R_4$ are independently selected from the group consisting of an optionally substituted alkyl, an optionally substituted cycloalkyl, and an optionally substituted arylalkyl. Preferably, each of $R_3$ and $R_4$ are independently an optionally substituted $C_{1-6}$ alkyl, an optionally substituted $C_{2-5}$ alkyl, or an optionally substituted $C_{3-4}$ alkyl. In one or more embodiments, each of $R_3$ and $R_4$ are independently selected from the group consisting of a methyl, an ethyl, and an isopropyl. In one embodiment, each of $R_3$ and $R_4$ are the same. In another embodiment, each of $R_3$ and $R_4$ are different. In a preferred embodiment, each of $R_3$ and $R_4$ are a methyl.

Gemini cationic surfactants typically contain two lipophilic tails and two lipophobic headgroups which are chemically bonded by a linker. The surface properties exhibited by a gemini cationic surfactant may be impacted by the chemical structure of the linker and the length of the lipophilic tails in the surfactant.

In formula (I) L is a linear or branched hydrocarbon linker. Preferably, L is a saturated hydrocarbon linker. In one or more embodiments, L is an optionally substituted $C_{7-16}$ alkylene, preferably an optionally substituted $C_{8-15}$ alkylene, preferably an optionally substituted $C_{9-14}$ alkylene, preferably an optionally substituted $C_{10-13}$ alkylene, preferably an optionally substituted $C_{11-12}$ alkylene. In preferred embodiments, L is an optionally substituted $C_{8-12}$ alkylene, an optionally substituted $C_{9-11}$ alkylene, or an optionally substituted $C_{10}$ alkylene. The carbon counts described herein refer to a number of carbon atoms of the alkylene chain of L which excludes the carbon atoms of optionally present substituents.

In one embodiment, L is an unsubstituted alkylene, preferably a linear alkylene, preferably a linear $C_{7-16}$ alkylene, preferably a linear $C_{8-15}$ alkylene, preferably a linear $C_{9-14}$ alkylene, preferably a linear $C_{10-13}$ alkylene, preferably a linear $C_{11-12}$ alkylene. For example, L is —$(CH_2)_7$—, —$(CH_2)_8$—, —$(CH_2)_9$—, —$(CH_2)_{10}$—, —$(CH_2)_{11}$—, —(CH$_2$)$_{12}$—, —(CH$_2$)$_{13}$—, —(CH$_2$)$_{14}$—, —(CH$_2$)$_{15}$—, and —(CH$_2$)$_{16}$—. Alternatively, L is a branched alkylene, such as —(CH$_2$)$_2$CH(CH$_3$)—(CH$_2$)$_5$—, —(CH$_2$)$_4$CH(CH$_3$)—(CH$_2$)$_5$—, —CH(CH$_3$)—(CH$_2$)$_{11}$—, and —CH$_2$CH(CH$_3$)—(CH$_2$)$_{10}$—. L may be a cycloalkylene such as

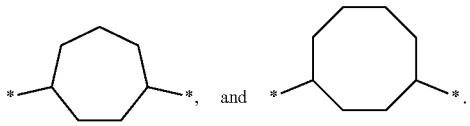

In a preferred embodiment, L is selected from the group consisting of —(CH$_2$)$_8$—, —(CH$_2$)$_{10}$—, and —(CH$_2$)$_{12}$—. Most preferably, L is —(CH$_2$)$_{12}$—. In at least one embodiment, L is not an optionally substituted C$_{1-6}$ alkylene (e.g., an optionally substituted C$_{2-5}$ alkylene, an optionally substituted C$_{3-4}$ alkylene).

As used herein, the value of x denotes an alkyl chain of —CH$_2$— groups connected to the —CH$_3$ end group of the surfactant of formula (I). In one or more embodiments, each of x is an integer in a range of 5-21, preferably 7-20, preferably 9-19, preferably 11-18, preferably 13-17, preferably 15-16. Most preferably, each of x is an integer in a range of 11-13, such as 11, 12, and 13.

As used herein, the value of y denotes an alkyl chain of —C(R$_1$)(R$_2$)— groups of the surfactant of formula (I). In one or more embodiments, each of y is an integer in a range of 2-5, preferably 3-4. Most preferably, each of y is 3.

As used herein, the value of n denotes the degree of ethoxylation (—O(CH$_2$)$_2$—) of the surfactant of formula (I). In one or more embodiments, each of n is an integer in a range of 1-15, preferably 2-14, preferably 3-13, preferably 4-12, preferably 5-11, preferably 6-10, preferably 7-9. In a preferred embodiment, each of n is an integer in a range of 2-11, 4-9, or 6-8. Most preferably, each of n is in a range of 6-11, 7-10, or 8-9. It is equally envisaged that the surfactant disclosed herein may have values for each of x, y, and/or n that fall outside of the aforementioned preferred ranges and still provide suitable surfactants of formula (I).

The term "anion" means a negatively charged ion including, but not limited to, halides, such as fluoride, chloride, bromide, and iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, tetrafluoroborate, hexafluorophosphate, and hexafluoroacetylacetonate. In one embodiment, X of the surfactant of formula (I) is an anion selected from the group consisting of a halide ion, a hexafluorophosphate ion, a trifluoromethanesulfonate ion, and a tetrafluoroborate ion. In a preferred embodiment, X is halide, such as chloride, bromide, fluoride, and iodide. In at least one embodiment, X is bromide or chloride. Most preferably, X is bromide.

In one or more embodiments, the surfactant used by the method disclosed herein is selected from the group consisting of:

a surfactant represented by formula (II)

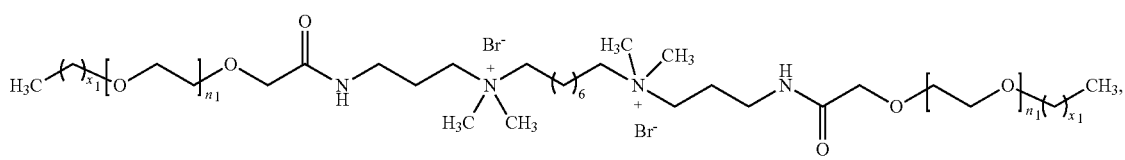

a surfactant represented by formula (III)

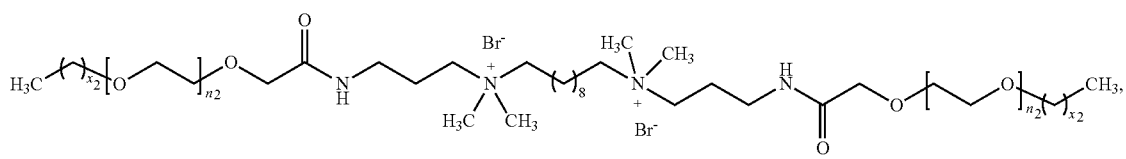

and
a surfactant represented by formula (IV)

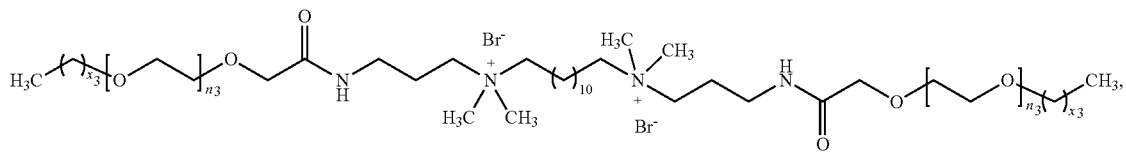

wherein each of $n_1$, $n_2$, and $n_3$ are independently an integer in a range of 1-15, preferably 2-14, preferably 3-13, preferably 4-12, preferably 5-11, preferably 6-10, preferably 7-9, or 8, and each of $x_1$, $x_2$, and $x_3$ are independently an integer in a range of 5-21, preferably 7-20, preferably 9-19, preferably 11-18, preferably 13-17, preferably 15-16. Most preferably, each of $n_1$, $n_2$, and $n_3$ are independently an integer in a range of 6-11, 7-10, or 8-9. For example, each of $n_1$, $n_2$, and $n_3$ are independently 9, 10, or 11. In a related embodiment, each of $x_1$, $x_2$, and $x_3$ are independently an integer in a range of 11-13, such as 11, 12, and 13.

In preferred embodiments, the surfactant used herein is represented by formula (IV), where each of $n_3$ and $x_3$ are in accordance with the ranges specified above.

In one embodiment, the surfactant used by the method of the present disclosure has a number average molecular weight (Mn) of 650-6,000 g/mol, preferably 700-5,000 g/mol, preferably 750-4,000 g/mol, preferably 800-3,500 g/mol, preferably 900-3,000 g/mol, preferably 1,000-2,750 g/mol, preferably 1,200-2,500 g/mol, preferably 1,500-2,000 g/mol. However, in certain embodiments, the surfactant has an average molecular weight that is greater than 6,000 g/mol.

In one or more embodiments, the surfactant of the present disclosure is soluble in water at a temperature of 4-90° C., 10-60° C., 20-40° C., or 25-35° C. The water may be tap water, distilled water, bidistilled water, deionized water, deionized distilled water, reverse osmosis water, and/or some other water. Most preferably the water is deionized water.

The method disclosed herein may be applicable to any subterranean geological formation including a shale formation, a clay formation, a carbonate formation, a sandstone formation, or like formation. In preferred embodiments, the subterranean geological formation is a shale formation, which contains clay minerals and quartz. In another preferred embodiment, the subterranean geological formation is a clay formation, which contains chlorite, illite, kaolinite, montmorillonite and smectite. In some embodiments, the subterranean geological formation is a carbonate formation, e.g. limestone or dolostone, which contains carbonate minerals, such as calcite, aragonite, dolomite, etc., or a sandstone formation, for example, a formation which contains quartz, feldspar, rock fragments, mica and numerous additional mineral grains held together with silica and/or cement.

Exemplary types of clay mineral present in subterranean geological formations include, but are not limited to, smectite, kaolin, illite, chlorite, sepiolite, attapulgite, or some other type. Smectites include dioctahedral smectites such as montmorillonite, nontronite, bentonite, and beidellite, as well as trioctahedral smectites such as saponite, hectorite, and stevensite. Kaolins include the minerals kaolinite, dickite, halloysite, and nacrite. Illites include clay-micas and illite. Chlorites include baileychlore, chamosite, clinochlore, cookeite, donbassite, gonyerite, nimite, odinite, orthochamosite, pennantite, ripidolite, and sudoite.

Clays (e.g., bentonite) and other subterranean shales can degrade, such as swell or crack, when exposed to water. During drilling operations, the tendency for clay to adsorb water from an aqueous downhole fluid, such as an aqueous drilling fluid and fracturing fluid, can lead to significant swelling of the clay. Clay swelling may cause decreased wellbore size, wellbore instability, and swollen cuttings which in turn lead to bit balling and poor penetration. For example, smectite clay minerals (e.g., bentonite), which have a large cation exchange capacity, tend to swell when contacted with water, thereby reducing formation permeability. The swelling can also cause smectite to disperse into platelets which can then migrate and block passageways to the wellbore.

Swellable clays that can be stabilized by the methods disclosed herein include, but are not limited to, smectite clays (e.g., montmorillonite, bentonite, beidellite, nontronite, saponite, hectorite, stevensite, and sauconite), kaolin clays (e.g., kaolinite, nacrite, dickite, endellite, and halloysite), illite clays (e.g., hydrobiotite, glauconite, illite), chlorite clays (e.g., chamosite), and other clay minerals not belonging to the above groups such as vermiculite, palygorskite, sepiolite, and mixed-layer (both regular and irregular) varieties of the above clay minerals. Bentonite clays may include a mixture of clay species such as montmorillonite, illite, and/or kaolinite. Bentonite clays may contain at least 60 wt % of a montmorillonite with a general empirical formula of $(Na,Ca)_{0.33}(Al,Mg)_2(Si_4O_{10})(OH)_2$, preferably at least 70 wt %, more preferably at least 80 wt % of the montmorillonite relative to a total weight of the bentonite.

In one or more embodiments, the swellable clay that can be stabilized by the methods disclosed herein is at least one selected from the group consisting of a smectite clay, a kaolin clay, an illite clay, and a chlorite clay, and a sepiolite clay. In preferred embodiments, the swellable clay is a smectite clay. More preferably, the swellable clay is a smectite clay that comprises montmorillonite. Most preferably, the swellable clay is bentonite.

It is equally envisaged that the method disclosed herein may be used to stabilize other water-sensitive materials present in subterranean geological formations in addition to, or in lieu of the swellable clays. Non-limiting examples of additional water-sensitive materials that can be stabilized by the present method include silica, iron minerals, alkaline earth metal carbonates, feldspars, and mixtures thereof.

Interaction of treatment fluids (e.g., drilling fluid) with reservoir rock (e.g. shale rock, clay formation) can lead to destabilization of the wellbore and formation damage and significant reduction of hydrocarbon production. Major issues involved in utilizing water-based treatment fluids include borehole enlargement and shale sloughing, which severely damage the wellbore formation. Ideally, a treatment fluid formulation should be inactive towards the reservoir rock in order to preserve the integrity of the wellbore and minimize the invasion of the drilling fluid into the formation. The selection of treatment fluid components is crucial in minimizing the shale dispersion and maximizing the pore plugging in the wellbore formation.

The surfactants described herein may be especially suitable as a clay swelling inhibitor. The surfactants may be also used in formulating detergents, which can include one or more conventional additives such as buffers, abrasives, bleaching agent, brighteners, fragrances, dyes, antistatic agents, antimicrobial agents, enzymes, and the like. As discussed below, treating swellable clays with the surfactants of formula (I), or a solvate thereof, a tautomer thereof, a stereoisomer thereof, or a mixture thereof reduces the tendency of these clays to swell.

The method of stabilizing a subterranean geological formation containing a swellable clay involves treating the swellable clay in the formation with a composition that includes an effective amount of the surfactant of formula (I) described herein. The swellable clay in the formation may be treated with the composition that includes an effective amount of the surfactant of formula (I) via any suitable method including, but not limited to, contacting, infusing, saturating the swellable clay with the composition, and/or injecting the composition into the formation. The amount of the surfactant of formula (I) present in the composition may be varied depending on the drilling operations, wellbore conditions, and the nature of other components in the composition. However, typically, the surfactant described herein in any its embodiments is present in an amount of 0.001-5 wt. % relative to a total weight of the composition, preferably 0.005-4 wt. %, preferably 0.01-3 wt. %, preferably 0.015-2 wt. %, preferably 0.02-1 wt. %, preferably 0.025-0.5 wt. %, preferably 0.03-0.25 wt. %, preferably 0.035-0.2 wt. %, preferably 0.04-0.15 wt. %, preferably 0.045-0.1 wt. %, preferably 0.05-0.09 wt. %, preferably 0.055-0.08 wt. %, preferably 0.06-0.075 wt. % relative to a total weight of the composition. In one or more embodiments, the surfactant is present in an amount up to 0.075 wt. % relative to a total weight of the composition, preferably 0.025-0.06 wt. %, more preferably about 0.05 wt. % relative to a total weight of the composition.

In one or more embodiments, the composition further includes an aqueous base fluid. As used here, the term "aqueous base fluid" refers to any water containing solution, including saltwater, hard water, and/or fresh water. For purposes of this description, the term "saltwater" includes saltwater with a chloride ion content of between about 6000 ppm and saturation, and is intended to encompass seawater and other types of saltwater including groundwater comprising additional impurities typically found therein. The term "hard water" includes water having mineral concentrations between about 2000 mg/L and about 300,000 mg/L. The term "fresh water" includes water sources that comprise less than 6000 ppm, preferably less than 5000 ppm, preferably less than 4000 ppm, preferably less than 3000 ppm, preferably less than 2000 ppm, preferably less than 1000 ppm, preferably less than 500 ppm of salts, minerals, or any other dissolved solids. Exemplary salts that may be present in saltwater, hard water, and/or fresh water include, but are not limited to, cations such as sodium, magnesium, calcium, potassium, ammonium, and iron, and anions such as chloride, bicarbonate, carbonate, sulfate, sulfite, phosphate, iodide, nitrate, acetate, citrate, fluoride, and nitrite.

The aqueous base fluid may be supplied from a natural source, such as an aquifer, a lake, and/or an ocean, and may be filtered to remove large solids before being used in the drilling fluid. Alternatively, the aqueous base fluid may be produced water (byproduct of the oil industry), tap water, distilled water, doubly distilled water, deionized water, deionized distilled water, or combinations thereof. In at least one embodiment, the aqueous base fluid used herein is deionized water. The aqueous base fluid may be present in the composition in an amount of 40-99.999 wt. %, preferably 50-99.9 wt. %, preferably 60-99 wt. %, more preferably 70-95 wt. %, even more preferably 80-90 wt. %, relative to a total weight of the composition. In one embodiment, the composition of the present disclosure may be considered a water-based drilling fluid, fracturing fluid, completion fluid, and production fluid. The composition used by the method disclosed herein may be prepared by combining and mixing a known volume or weight of one or more surfactants of formula (I) and the optionally present aqueous base fluid via mixing procedures known to those of ordinary skill in the art.

In some embodiments, the composition disclosed herein may contain a non-aqueous phase in addition to or in lieu of the aqueous base fluid. Exemplary non-aqueous phases include, but are not limited to, oil phases such as diesel oil, petroleum oil, fuel oil, biodiesel, biomass to liquid (BTL) fuel, gas to liquid (GTL) diesel, mineral oil, an ester, an alpha-olefin, a natural oil, and derivatives and/or combinations thereof, and non-aqueous solvents such as chlorinated solvents (e.g. chlorobenzene, dichloromethane, 1,2-dichloroethane, 1,1-dichloroethane, chloroform, carbon tetrachloride), aromatic solvents (e.g., benzene, ethylbenzene, o-xylene, m-xylene, p-xylene, and mixtures of xylenes, toluene, mesitylene, anisole, 1,2-dimethoxybenzene, $\alpha,\alpha,\alpha$,-trifluoromethylbenzene, fluorobenzene, heavy aromatic naptha), alkane solvents (e.g., pentane, cyclopentane, hexanes, cyclohexane, heptanes, cycloheptane, octanes), ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), ester solvents (e.g. ethyl acetate, propyl acetate), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), as well as mixtures thereof. In one embodiment, the composition containing the surfactant of formula (I) may be considered as a non-aqueous composition.

The surfactant of formula (I) used herein effectively reduces or inhibits swelling (e.g., surface hydration, osmotic swelling) of clays and shales. The swelling characteristics of the composition containing the surfactant can be determined by a linear swelling percentage using a linear swell meter (see Example 6) and/or by a free swelling test (see Example 7). In general, the lower the swelling percentage and the longer the time to reach that swelling percentage indicate better clay swell inhibition.

The step of treating/contacting the swellable clay in a formation with the presently disclosed composition containing the surfactant of formula (I) results in a reduction in clay swelling compared with that resulting from treating/contacting the swellable clay with a composition devoid of the surfactant of formula (I). In one or more embodiments, the step of treating/contacting the swellable clay in a formation with the presently disclosed composition containing the surfactant of formula (I) results in clay swelling that is 7-50% less than that resulting from treating/contacting the swellable clay with a composition that is devoid of the surfactant (e.g., deionized water), preferably 10-45% less, preferably 15-40% less, more preferably 20-35% less, even more preferably 25-30% less than that resulting from a composition that is devoid of the surfactant over a exposure duration of 0.1-40 hours, 1-40 hours, 4-36 hours, 8-30 hours, or 12-24 hours (see FIGS. 3-5, and Table 1). In a related embodiment, a linear swelling percentage of about 100% is reached using the presently disclosed composition at least 3 hours slower than using a composition that is devoid of the surfactant of formula (I) (e.g., deionized water), preferably 4-12 hours slower, preferably 6-10 hours slower, preferably 7-8 hours slower than using the composition that is devoid of the surfactant (e.g., deionized water) (see FIGS. 3-5). An increase of the surfactant concentration in the composition up to about 0.05 wt. % generally leads to a more effective clay swell inhibition. However, further enhancement of the surfactant concentration above 0.05 wt. % show minimal or negative impact on the clay swelling inhibition of the composition (see FIGS. 3-5, and Table 1).

It is worth noting that the surfactant of formula (I) having a longer hydrocarbon linker (e.g., L is —(CH$_2$)$_{12}$—) yields greater clay swelling inhibition than the surfactant of formula (I) having a shorter hydrocarbon linker (e.g., L is —(CH$_2$)$_8$—, or —(CH$_2$)$_{10}$—). In one embodiment, clay swelling resulting from a composition containing the surfactant having the longer hydrocarbon linker (e.g., surfactant GS12) is 10-25% less than that resulting from a composition containing the surfactant having a shorter hydrocarbon linker (e.g., surfactant GS8, GS10), preferably 12-20% less, more preferably 14-18% less, even more preferably 15-16% less than that resulting from a composition containing the surfactant having a shorter hydrocarbon linker over a exposure duration of 0.1-40 hours, 1-40 hours, 4-36 hours, 8-30 hours, or 12-24 hours (see FIGS. 3-5, and Table 1). In a related embodiment, a linear swelling percentage of about 100% is reached using a composition containing the surfactant having a longer hydrocarbon linker (e.g., surfactant GS12) at least 2 hours slower than using a composition containing the surfactant having a shorter hydrocarbon linker (e.g., surfactant GS8, GS10), preferably 3-8 hours slower, preferably 4-7 hours slower, preferably 5-6 hours slower than using a composition containing the surfactant having a shorter hydrocarbon linker (see FIGS. 3-5).

Electrolytes such as NaCl and KCl are commonly employed to reduce clay swelling. However, these electrolytes can adversely affect the properties of drilling fluid. For example, the salts cause flocculation of clay minerals (e.g., bentonite), which results in high fluid losses. The presence of salts (e.g., potassium salts) in a drilling fluid also negatively impacts its rheology and thixotropy properties, and lowers its lifting capacity of shale cuttings of a drilling fluid. Drilling fluids containing high levels of potassium salts are toxic to the marine organisms and may pollute oil drilling and waste disposal areas. Further, KCl based drilling fluids can disintegrate shales with high swellable clay contents, coagulate the cuttings around drilling bit, and lead to bit balling [Ahmad, H. M.; Kamal, M. S.; Al-Harthi, M. A. Polymeric and low molecular weight shale inhibitors: A review. *Fuel* 2019; and Ahmad, H. M.; Kamal, M. S.; Mahmoud, M.; Hussain, S. S.; Abouelresh, M.; Al-Harthi, M. A. Organophilic clay-based drilling fluids for mitigation of unconventional shale reservoirs instability and formation damage. *Journal of Energy Resources Technology* 2019, 141, 093102].

Conventionally employed potassium salts for clay swelling inhibition include, but are not limited to, potassium chloride (KCl), potassium bromide (KBr), potassium formate, potassium fluoride, and potassium iodide. In preferred embodiments, the composition used herein is substantially free of a potassium salt, which includes being substantially free of, preferably completely free of (i.e., 0 wt. %) a potassium salt, such as KCl.

As discussed in Example 7, the use of the surfactant of formula (I) provides an unexpected result compared to a potassium salt (e.g., KCl), where the addition of the potassium salt does not enhance the clay swelling inhibition of the aqueous solution, and in some cases actually causes greater clay swelling than water. On the other hand, the surfactant of formula (I) exhibits significantly greater inhibition of clay swelling compared to water and an aqueous solution containing the potassium salt (see FIGS. 6A-C, 7A-C, 8A-C). Further, using the surfactant of formula (I) alone provides greater inhibition in clay swelling/disintegration than using a combination of the potassium salt and the surfactant (FIGS. 8A-C verse FIGS. 9A-C).

The composition used by the method of the present disclosure may optionally comprise any number of suitable additives. Exemplary additives include, but are not limited to, weighting agents, emulsifiers, viscosifier, fluid-loss control agents, bridging agents, pH controlling agents, defoamers, clay stabilizers, antiscalants, deflocculants, lubricants, gelling agents, corrosion inhibitors, rheology control modifiers or thinners, high temperature/high pressure control additives, acids, alkalinity agents, pH buffers, fluorides, gases, nitrogen, carbon dioxide, surface modifying agents, tackifying agents, foamers, catalysts, clay control agents, biocides, bactericides, friction reducers, antifoam agents, dispersants, flocculants, H$_2$S scavengers, CO$_2$ scavengers, oxygen scavengers, friction reducers, breakers, relative permeability modifiers, resins, particulate materials (e.g., proppant particulates), wetting agents, coating enhancement agents, filter cake removal agents, odorants, shale stabilizers, and the like. A person of ordinary skill in the art, with the benefit of this disclosure, will recognize the types and suitable amounts of additives that may be included in the composition for a particular application, without undue experimentation.

The composition containing the surfactant of formula (I) may be made to contact the swellable clays present in a subterranean geological formation via any suitable method that provides effective contact between the composition and the swellable clays. The swellable clays may be treated with the composition during one or more oil field operations including wellbore drilling through a formation, formation fracturing, formation acidizing, wellbore completion, and oil production from a producing formation. The composition may be used during or in conjunction with operations such as formation drilling, sand control treatments (e.g., gravel packing), formation fracturing (e.g., hydraulic fracturing), wellbore injecting, oil producing, wellbore completion or other operations performed on the subterranean geological formation. Use of the composition containing the surfactant of formula (I) during or in conjunction with drilling, fracturing, acidizing, completion, injection, and/or production operation helps to reduce the swelling and migration of the swellable clays, thereby stabilizing the subterranean geological formation.

The surfactant of formula (I) may be prepared via a method depicted by FIG. 1. Specifically, the method may involve mixing a carboxylic acid of formula (V)

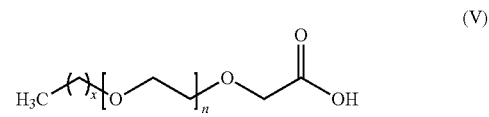

(V)

or a salt thereof, a solvate thereof, or a mixture thereof with an amine of formula (VI)

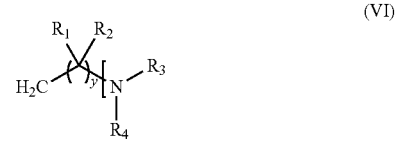

(VI)

or a salt thereof, a solvate thereof, a stereoisomer thereof, or a mixture thereof in the presence of a fluoride salt to form a mixture, heating the mixture to obtain an amidoamine intermediate, and reacting the amidoamine intermediate with a disubstituted hydrocarbon linker of formula (VII)

(VII)

or a solvate thereof, a stereoisomer thereof, or a mixture thereof in a solvent, thereby forming the surfactant, wherein (i) $R_1$ and $R_2$ are independently selected from the group consisting of a hydrogen, an optionally substituted alkyl, an optionally substituted cycloalkyl, and an optionally substituted arylalkyl, (ii) $R_3$ and $R_4$ are independently selected from the group consisting of an optionally substituted alkyl, an optionally substituted cycloalkyl, and an optionally substituted arylalkyl, (iii) L is a $C_{7-16}$ alkylene, (iv) x is an integer in a range of 5-21, (v) y is an integer in a range of 2-5, (vi) n is an integer in a range of 1-15, and (vii) Y is a halogen.

In one or more embodiments, x of the carboxylic acid of formula (V) is an integer in a range of 5-21, preferably 7-20, preferably 9-19, preferably 11-18, preferably 13-17, preferably 15-16. Most preferably, x is an integer in a range of 11-13, for example 11, 12, and 13. In related embodiments, n of the carboxylic acid of formula (V) is an integer in a range of 1-15, preferably 2-14, preferably 3-13, preferably 4-12, preferably 5-11, preferably 6-10, preferably 7-9. In a preferred embodiment, n is an integer in a range of 2-11, 4-9, or 6-8. Most preferably, n is in a range of 6-11, 7-10, or 8-9.

Exemplary carboxylic acids that may be used herein include, but are not limited to, glycolic acid ethoxylate lauryl ether, glycolic acid ethoxylate hexyl ether, glycolic acid ethoxylate heptyl ether, glycolic acid ethoxylate octyl ether, glycolic acid ethoxylate nonyl ether, glycolic acid ethoxylate decyl ether, glycolic acid ethoxylate tetradecyl ether, glycolic acid ethoxylate hexadecyl ether, glycolic acid ethoxylate stearyl ether, glycolic acid ethoxylate nonadecyl ether, glycolic acid ethoxylate eicosyl ether, and glycolic acid ethoxylate heneicosyl ether. In one or more embodiments, the carboxylic acid of formula (V) has a number average molecular weight of 250-900 g/mol, preferably 300-850 g/mol, preferably 350-800 g/mol, preferably 400-750 g/mol, preferably 450-700 g/mol, preferably 500-650 g/mol, preferably 550-600 g/mol. In one embodiment, the carboxylic acid is glycolic acid ethoxylate lauryl ether with a number average molecular weight of about 360 g/mol. In a most preferred embodiment, the carboxylic acid is glycolic acid ethoxylate lauryl ether with a number average molecular weight of about 690 g/mol. The glycolic acid ethoxylate lauryl ether may be available from commercial vendors such as Sigma Aldrich.

In one or more embodiments, $R_1$ and $R_2$ of the amine of formula (VI) are independently selected from the group consisting of a hydrogen and a methyl. In a preferred embodiment, $R_1$ and $R_2$ are a hydrogen. In a related embodiment, $R_3$ and $R_4$ of the amine of formula (VI) are independently selected from the group consisting of a methyl, an ethyl, and an isopropyl. In a preferred embodiment, $R_3$ and $R_4$ are a methyl. In another related embodiment, y of the amine of formula (VI) is an integer in a range of 2-5, preferably 3-4. In a preferred embodiment, y is 3. In a most preferred embodiment, the amine of formula of (VI) is 3-(dimethylamino)-1-propylamine. Other amines that may be used in addition to or in lieu of 3-(dimethylamino)-1-propylamine include, but are not limited to, 2-(dimethylamino)ethylamine, 2-(diethylamino)ethylamine, 1-dimethylamino-2-propylamine, 3-(diethylamino)propylamine, (3-amino-2-methylpropyl)dimethylamine, (3-amino-1-methylpropyl)dimethylamine, N,N,2,2-tetramethyl-1,3-propanediamine, 4-(dimethylamino)butylamine, 5-(dimethylamino)amylamine, 5-(diethylamino)pentylamine, and 5-(diisopropylamino)amylamine.

The method of the present disclosure may involve an amidation reaction of the mixture comprising the carboxylic acid of formula (V) and the amine of formula (VI) to produce a corresponding amidoamine intermediate of formula (VIII)

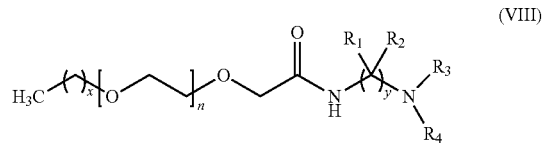
(VIII)

or a salt thereof, a solvate thereof, a stereoisomer thereof, or a mixture thereof, wherein values for x and n are consistent with those described for the carboxylic acid of formula (V), and $R_1$, $R_2$, $R_3$, and $R_4$, as well as value for y are consistent with those described for the amine of formula (VI).

In a preferred embodiment, reacting the mixture comprising the carboxylic acid of formula (V) with the amine of formula (VI) is conducted in neat (solvent-free) condition. It is equally envisaged that the reaction may be adapted to be performed in a solvent such as benzene, xylene, dimethylformamide, tetrahydrofuran, ethyl acetate, diethyl ether, acetonitrile, dimethyl sulfoxide, methylene chloride, chloroform, nitrobenzene, isopropanol, and mixtures thereof. In a preferred embodiment, a molar ratio of the amine of formula (VI) to the carboxylic acid of formula (V) is in a range of 1:1 to 5:1, preferably 1:2 to 1:4, or about 2:7. In some embodiments, the amine is introduced to the mixture in a two-stage or multi-stage fashion. For example, a first portion of the amine which is 50-70%, 55-65%, or about 57% of a total mole of the amine used herein may be added to the mixture and allowed to react with the carboxylic acid for 3-9 hours, 5-7 hours, or about 6 hours, and subsequently a second portion of the amine which is 30-50%, 35-45%, or about 43% of a total mole of the amine used herein may be added to the same mixture and allowed to react with the carboxylic acid for 2-8 hours, 4-6 hours, or about 5 hours. Alternatively, the amine may be introduced to the mixture in one batch and allowed to react with the carboxylic acid for 5-20 hours, 8-15 hours, or about 12 hours.

In one or more embodiments, the aforementioned mixture is heated at a temperature of 50-200° C., preferably 100-190° C., preferably 120-180° C., preferably 130-170° C., preferably 150-160° C. under agitation. An external heat source, such as an oil bath, an oven, microwave, or a heating mantle, may be employed to heat the mixture. The mixture may be agitated throughout the duration of the reaction by employing a rotary shaker, a magnetic stirrer, or an overhead stirrer. In another embodiment, the mixture is left to stand (i.e. not agitated). In one embodiment, the mixture is sonicated in an ultrasonic bath or with an ultrasonic probe. The amidation reaction may be conducted in inert gas (e.g. nitrogen, argon, helium). Also, in some embodiments, the reaction may not be conducted in inert gas, but in a vacuum. In a preferred embodiment, the intermediate of formula (VIII) is collected as an oil that may be separated and washed in acetone, ethyl acetate, and/or isopropanol and then dried. In one embodiment, the oil may be dried under vacuum until a constant weight is achieved. In a preferred embodiment, the step forming the intermediate of formula (VIII) has a product yield of at least 75%, preferably at least 80%, preferably at least 90%, preferably at least 92%, preferably at least 94%, preferably at least 96%, preferably at least 97%.

In one or more embodiments, the mixture comprises a fluoride salt. The fluoride salt may be present as a catalyst to accelerate the amidation reaction. In a preferred embodiment, the fluoride salt used herein is at least one selected from the group consisting of sodium fluoride, potassium fluoride, silver fluoride, cesium fluoride, and tetrabutylammonium fluoride. In a most preferred embodiment, the fluoride salt is sodium fluoride. In one or more embodiments, a molar ratio of the fluoride salt to the carboxylic acid is in the range of 1:5 to 1:20, preferably 1:6 to 1:18, preferably 1:8 to 1:15, preferably 1:9 to 1:12, or about 1:10. Other amide bond formation reagents and catalysts that may be used in addition to or in lieu of the fluoride salt include, but are not limited to, carbodiimides such as 1-ethyl-3-(3-dimethylaminopropyl)carbodiimide (EDC), N,N-dicyclohexylcarbodiimide (DCC), 1H-benzotriazole derivatives such as 1-[bis(dimethylamino)methylene]-1H-1,2,3-triazolo[4,5-b]pyridinium 3-oxid hexafluorophosphate (HATU), O-(benzotriazol-1-yl)-1,1,3,3-tetramethyluronium hexafluorophosphate (HBTU), O-benzotriazol-1-yl-1,1,3,3-tetramethyluronium tetrafluoroborate (TBTU), as well as phosphoric acid, sulfuric acid, boric acid, silica gel, and zeolite.

In one or more embodiments, the mixture further comprises a molecular sieve. The molecular sieve may facilitate the removal of by-product (i.e., water) produced during the amidation reaction. Non-limiting exemplary molecular sieves applicable to the method disclosed herein include aluminosilicate minerals, porous glass, activated carbon, clay, and mesoporous silica. In a preferred embodiment, the molecular sieve comprises aluminum oxide ($Al_2O_3$). In a most preferred embodiment, the molecular sieve comprises microporous aluminum oxide having an average pore size of 0.2-0.5 nm, or 0.3-0.4 nm. Other drying agents that may be used in addition to or in lieu of the molecular sieve include, but are not limited to zeolites, anhydrous sodium sulfate, anhydrous magnesium sulfate, anhydrous calcium chloride, and anhydrous calcium sulfate. Conventional water removing apparatus such as Dean-Stark trap may be utilized in addition to the aforementioned drying agents.

In one or more embodiments, L of the disubstituted hydrocarbon linker of formula (VII) is an optionally substituted alkylene (e.g., an optionally substituted $C_{7-16}$ alkylene, an optionally substituted $C_{8-15}$ alkylene, an optionally substituted $C_{9-14}$ alkylene, an optionally substituted $C_{10-13}$ alkenylene, an optionally substituted $C_{11-12}$ alkenylene. In preferred embodiments, L is selected from the group consisting of —$(CH_2)_8$—, —$(CH_2)_{10}$—, and —$(CH_2)_{12}$—. Most preferably, L is —$(CH_2)_{12}$—. In one embodiment, Y is a halogen, preferably a chloro, a bromo, or an iodo. Preferably, Y is a bromo or chloro. For example, the disubstituted hydrocarbon linker of formula (VII) may be selected from 1,8-dibromooctane, 1,10-dibromodecane, and 1,12-dibromododecane. In a most preferred embodiment, the disubstituted hydrocarbon linker of formula (VII) is 1,12-dibromododecane.

The method disclosed herein also involves reacting the amidoamine intermediate of formula (VIII) with the disubstituted hydrocarbon linker of formula (VII), thereby producing the surfactant of formula (I).

In a preferred embodiment, reacting the amidoamine intermediate with the disubstituted hydrocarbon linker is conducted in a polar aprotic solvent, preferably ethyl acetate. Exemplary polar aprotic solvents that may be used in addition to or in lieu of ethyl acetate include dimethylformamide, tetrahydrofuran, acetone, acetonitrile, and dimethyl sulfoxide. It is equally envisaged that the reaction may be adapted to be performed in polar protic solvent such as methanol, ethanol, n-propanol, isopropyl alcohol, n-butanol, and mixtures thereof. In certain embodiments, reacting the amidoamine intermediate with the disubstituted hydrocarbon linker is conducted without a solvent.

In a preferred embodiment, the reacting is performed at a concentration of the disubstituted hydrocarbon linker in a range of 0.01-10 M, preferably 0.05-5 M, preferably 0.1-2 M, preferably 0.8-1.2 M. In a preferred embodiment, a molar ratio of the amidoamine intermediate to the disubstituted hydrocarbon linker is in a range of 1.5:1 to 5:1, preferably 2:1 to 4:1, or about 2.5:1. In a preferred embodiment, the aforementioned reacting is conducted under agitation at a temperature of up to 120° C., preferably 50-100° C., preferably 60-95° C., preferably 70-90° C., preferably 75-85° C., or about 80° C. and has a reaction time of up to 96 hours, preferably 6-72 hours, preferably 12-60 hours, preferably 30-54 hours, or about 48 hours. The surfactant may be isolated and purified from the reaction mixture by methods known to those of ordinary skill in the art such as distillation, crystallization, column chromatography, and high pressure liquid chromatography (HPLC) (normal phase or reversed phase). Preferred methods include, purifying the reaction mixture with column chromatography (with silica or alumina as the stationary phase), preparative thin layer chromatography, and recrystallization. In one embodiment, the surfactant is purified with a silica gel column. In a preferred embodiment, the step forming the surfactant has a product yield of at least 80%, preferably at least 83%, preferably at least 85%, preferably at least 87%, preferably at least 89%, preferably at least 95%.

The method disclosed herein may further involve an ion-exchange reaction when X is an anion other than a halide ion. For example, after reacting the amidoamine intermediate of formula (VIII) with the disubstituted hydrocarbon linker of formula (VII), the product obtained may be subjected to an ion-exchange reaction with desirable salts comprising X anions such as hexafluorophosphate ions, trifluoromethanesulfonate ions, and tetrafluoroborate ions using methods known to those of ordinary skill in the art.

The examples below are intended to further illustrate protocols for preparing, characterizing the surfactants of formula (I), the compositions containing the surfactant, and uses thereof, and are not intended to limit the scope of the claims.

Example 1

Synthesis of Cationic Gemini Surfactants

Three cationic gemini surfactants (GS8, GS10, GS12) were synthesized and tested for their clay swelling inhibition capacity. These surfactants are structurally different by having spacers of various lengths. The spacers of GS8, GS10, and GS12 surfactants each contain 8, 10, and 12 carbon atoms.

The exemplary synthesis procedure of the cationic gemini surfactants is given in FIG. 1. The gemini surfactants were prepared by solvent-free amidation reaction of glycolic acid ethoxylate lauryl ether with 3-(dimethylamino)-1-propylamine, followed by a reaction with an appropriate dibromoalkane.

Glycolic acid ethoxylate lauryl ether used herein was purchased from Sigma Aldrich (CAS number: 220622-96-8, linear formula: $CH_3(CH_2)_{11-13}(OCH_2CH_2)$—$OCH_2CO_2H$, average Mn~690).

Example 2

Structure Characterization of Surfactant GS8

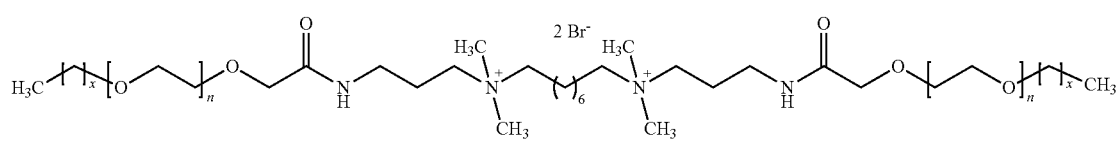

Viscous material (87% yield). $^1H$ NMR (CDCl$_3$, 500 MHz, δ in ppm): 0.88 (2×CH$_3$, t, J=6.7 Hz, (CH$_3$)$_2$), 1.16-1.36 ((CH$_2$)$_n$, m), 1.47-1.67 (4×CH$_2$, m), 1.85-1.91 (2×CH$_2$, m), 2.01-2.08 (2×CH$_2$, m), 3.22 (4×CH$_3$, s), 3.40-3.48 ((CH$_2$)$_n$, m), 3.48-3.75 (m, (OCH$_2$CH$_2$)$_n$), 4.03 (m, (CH$_2$)$_2$), 7.97 (2×NH). $^{13}C$ NMR (CDCl$_3$, 125 MHz, δ in ppm): 14.0, 22.6, 25.9, 29.2, 29.4, 29.5, 31.8, 35.7, 51.1, 62.1, 64.6, 70.4, 170.9. FTIR (υ in cm$^{-1}$) 3409 ($υ_{N-H}$), 2920 ($υ_{C-H}$ asymmetric), 2853 ($υ_{C-H}$ symmetric), 1628 (amide [I]), 1545 (amide [II]), 1464, 1348, 1097 (C—O—C stretching vibration), 945. MALDI-TOF MS m/z 768.5.

Example 3

Structure Characterization of Surfactant GS10

Viscous material (89% yield). $^1H$ NMR (CDCl$_3$, 500 MHz, δ in ppm): 0.88 (2×CH$_3$, t, J=6.7 Hz, (CH$_3$)$_2$), 1.16-1.36 ((CH$_2$)$_n$, m), 1.47-1.67 (4×CH$_2$, m), 1.70-1.78 (2×CH$_2$, m), 2.05-2.13 (2×CH$_2$, m), 3.27 (4×CH$_3$, s), 3.41-3.49 ((CH$_2$)$_n$, m), 3.50-3.77 (m, (OCH$_2$CH$_2$)$_n$), 4.03 (m, (CH$_2$)$_2$), 7.98 (2×NH). $^{13}C$ NMR (CDCl$_3$, 125 MHz, δ in ppm): 14.0, 22.5, 26.0, 29.2, 29.3, 29.4, 31.8, 35.6, 51.1, 62.1, 64.5, 70.4, 170.8. FTIR (υ in cm$^{-1}$) 3412 ($υ_{N-H}$), 2921 ($υ_{C-H}$ asymmetric), 2855 ($υ_{C-H}$ symmetric), 1627 (amide [I]), 1542 (amide [II]), 1463, 1347, 1096 (C—O—C stretching vibration), 946. MALDI-TOF MS m/z 724.5.

Example 5

Swelling Tests: Experimental

A compactor was used to prepare the sample in wafer form for study of expansion of the clay swelling. Two wafer samples can be prepared in the compactor at the same time. In the present disclosure, sodium based bentonite wafers were prepared to study the swelling inhibition property of the surfactants. Bentonite was chosen because it contains highly swellable clay mineral called montmorillonite, which

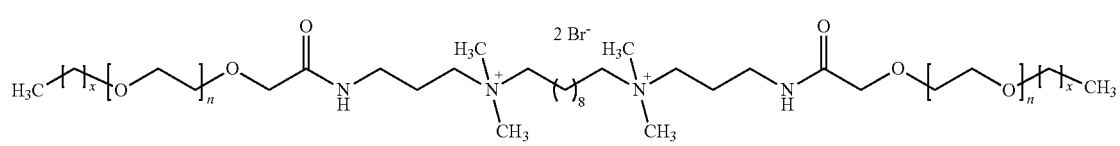

Viscous material (83% yield). $^1H$ NMR (CDCl$_3$, 500 MHz, δ in ppm): 0.88 (2×CH$_3$, t, J=6.7 Hz, (CH$_3$)$_2$), 1.16-1.36 ((CH$_2$)$_n$, m), 1.47-1.67 (4×CH$_2$, m), 1.73-1.79 (2×CH$_2$, m), 2.02-2.09 (2×CH$_2$, m), 3.25 (4×CH$_3$, s), 3.41-3.49 ((CH$_2$)$_n$, m), 3.50-3.77 (m, (OCH$_2$CH$_2$)$_n$), 4.03 (m, (CH$_2$)$_2$), 7.97 (2×NH). $^{13}C$ NMR (CDCl$_3$, 125 MHz, δ in ppm): 13.9, 22.5, 25.9, 29.2, 29.3, 29.5, 31.7, 35.7, 51.0, 62.0, 64.4, 70.3, 170.9. FTIR (υ in cm$^{-1}$) 3411 ($υ_{N-H}$), 2922 ($υ_{C-H}$ asymmetric), 2851 ($υ_{C-H}$ symmetric), 1631 (amide [II]), 1544 (amide [II]), 1465, 1350, 1099 (C—O—C stretching vibration), 947. MALDI-TOF MS m/z 680.2.

Example 4

Structure Characterization of Surfactant GS12 helps clearly illustrating the swelling phenomenon of clay and accurately determining swelling inhibitions of the surfactants.

The linear swelling test involved the following steps:

(i) The receiver in the large open end of the cell body with the solid end of the receiver facing the cell body was placed;

(ii) The assembly was inverted and the sample was poured into the small opening of the cell body. An amount of 12 g of sample powder was poured in the cell body;

(iii) A 14 mm spacer was inserted in the cell body so that it rested on top of the sample;

(iv) Piston was inserted to rest the small end on top of the spacer. Also, the large expanded end was positioned approximately 6-10 mm above the top of the cell body;

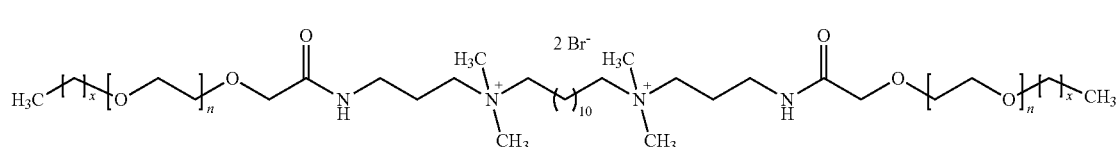

Figure 2:
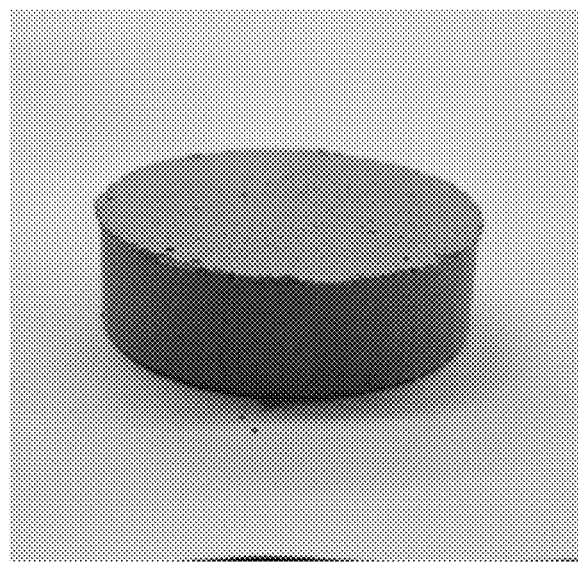
FIG. 2 is a picture showing a neat sample of a bentonite wafer prepared using a compactor.

(v) The cell assembly was loaded in the compactor, and 6000 psi pressure was applied using a hand pump for 30 min;

(vi) At the end of 30 min, the pressure was released, and the wafer was removed from the cell body. The wafer sample is shown in FIG. 2;

(vii) The wafer was loaded in the cup assembly. 150 mL of an aqueous fluid (e.g., deionized water, aqueous drilling fluids) was poured into the cup assembly, which was then stirred at 100 RPM (revolutions per minute) throughout the period of testing. The swelling test was conducted for 40 hours at room temperature and ambient pressure using a dynamic swell tester (model No. 150-80-1, manufactured by OFITE). At the end of the test, the swelling percentage was automatically calculated by the software.

Example 6

Linear Clay Swelling Results

Figure 3:
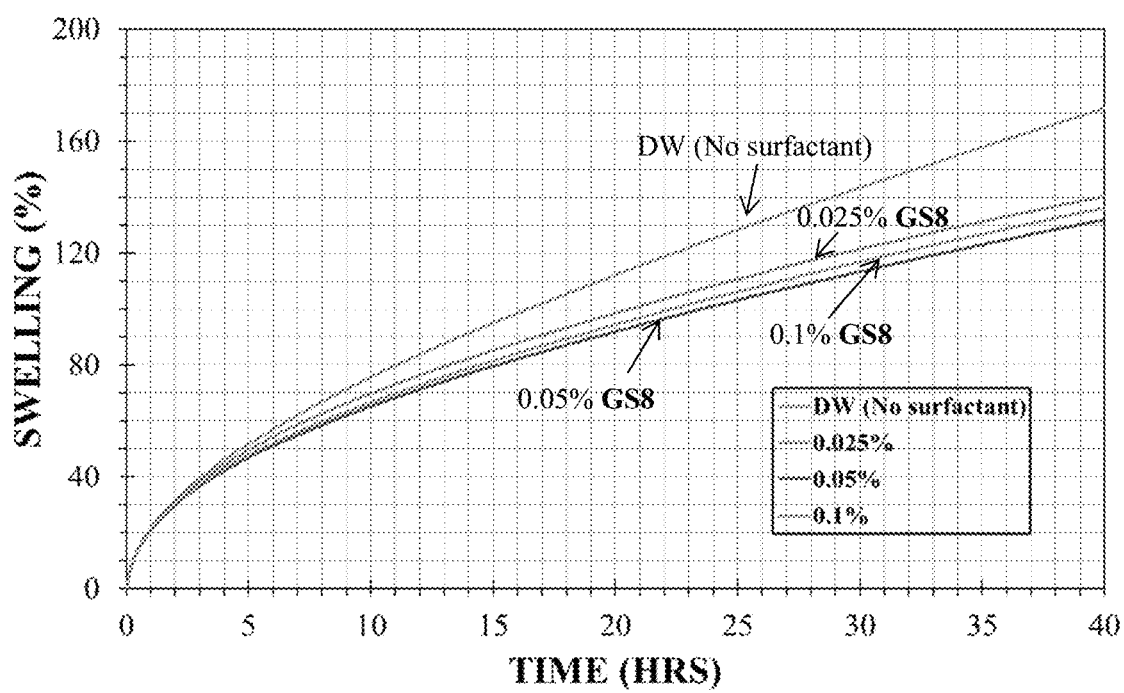
FIG. 3 is an overlay of linear swellings of clay over a period of 40 hours when exposed to deionized water (DW), an aqueous composition containing 0.025 wt. % of surfactant GS8 (0.025% GS8), an aqueous composition containing 0.05 wt. % of surfactant GS8 (0.05% GS8), and an aqueous composition containing 0.1 wt. % of surfactant GS8 (0.1% GS8), respectively.
Figure 4:
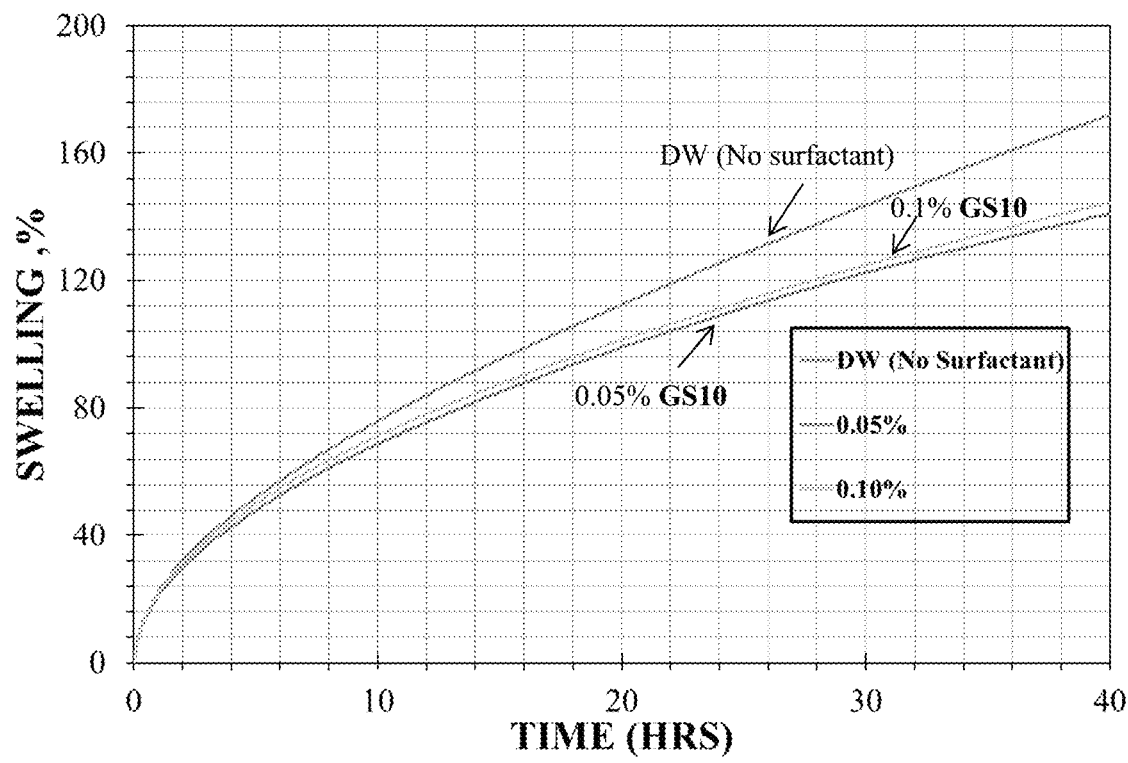
FIG. 4 is an overlay of linear swellings of clay over a period of 40 hours when exposed to deionized water (DW), an aqueous composition containing 0.05 wt. % of surfactant GS10 (0.05% GS10), and an aqueous composition containing 0.1 wt. % of surfactant GS10 (0.1% GS10), respectively.
Figure 5:
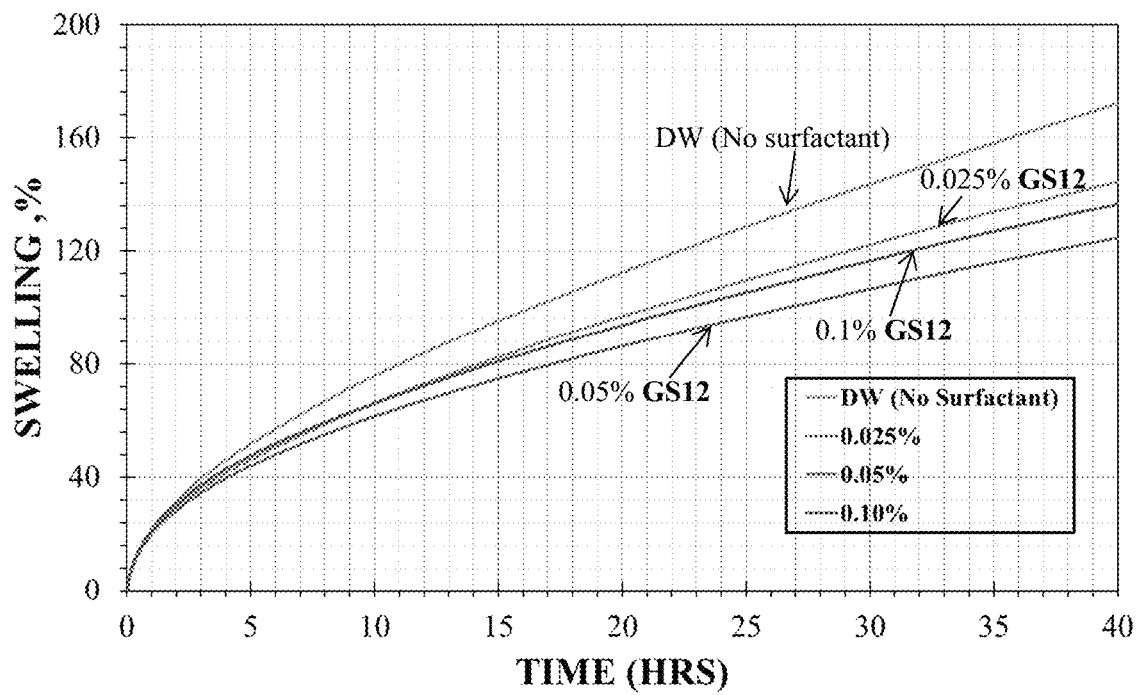
FIG. 5 is an overlay of linear swellings of clay over a period of 40 hours when exposed to deionized water (DW), an aqueous composition containing 0.025 wt. % of surfactant GS12 (0.025% GS12), an aqueous composition containing 0.05 wt. % of surfactant GS12 (0.05% GS12), and an aqueous composition containing 0.1 wt. % of surfactant GS12 (0.1% GS12), respectively.
Figure 6A:
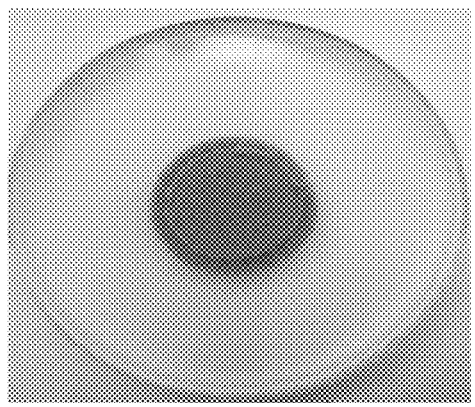
FIG. 6A is a picture of a bentonite wafer after being immersed in deionized water for 5 minutes.
Figure 6B:
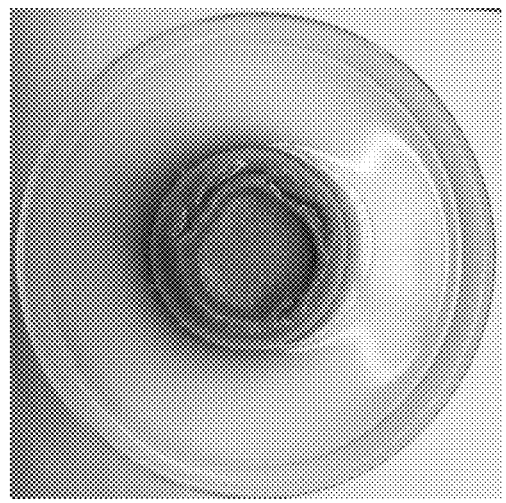
FIG. 6B is a picture of a bentonite wafer after being immersed in deionized water for 5 hours.
Figure 6C:
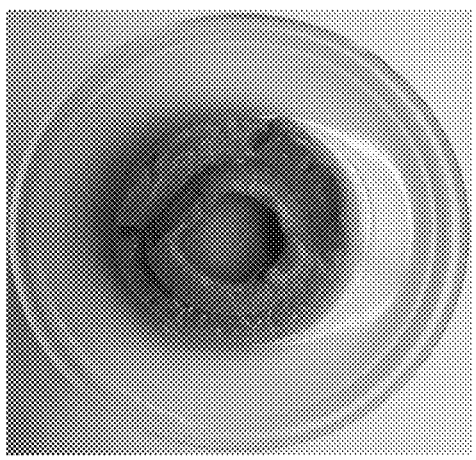
FIG. 6C is a picture of a bentonite wafer after being immersed in deionized water for 24 hours.
Figure 7A:
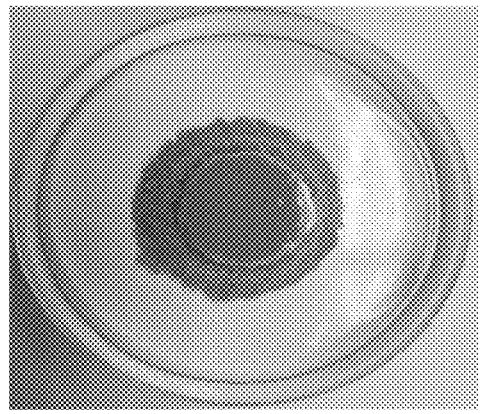
FIG. 7A is a picture of a bentonite wafer after being immersed in an aqueous solution containing 3 wt. % of KCl for 5 minutes.
Figure 7B:
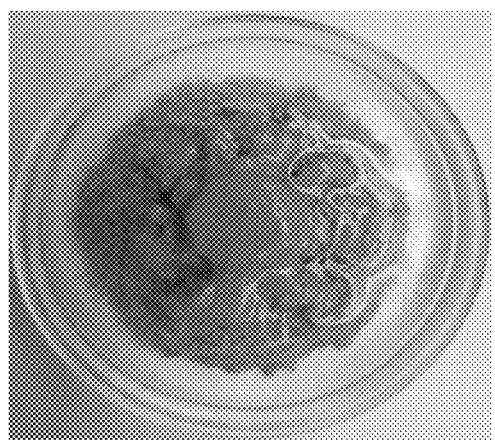
FIG. 7B is a picture of a bentonite wafer after being immersed in an aqueous solution containing 3 wt. % of KCl for 5 hours.
Figure 7C:
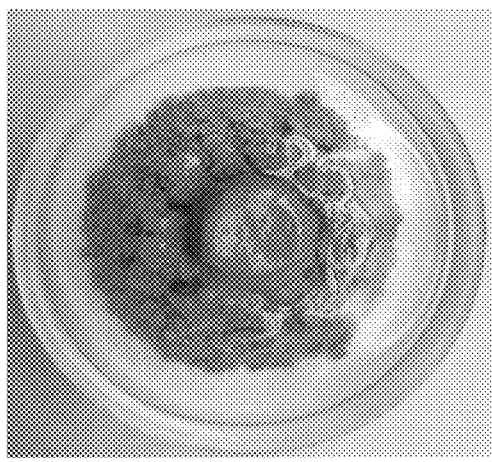
FIG. 7C is a picture of a bentonite wafer after being immersed in an aqueous solution containing 3 wt. % of KCl for 24 hours.
Figure 8A:
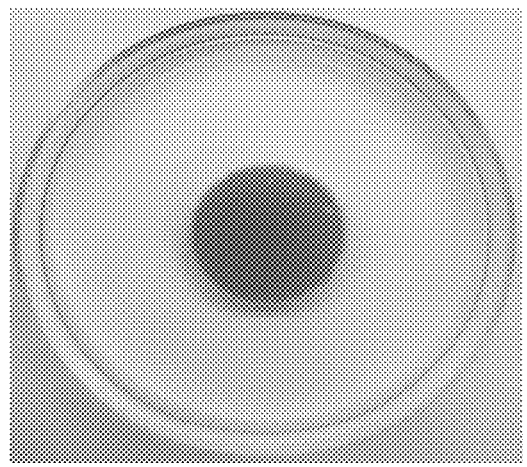
FIG. 8A is a picture of a bentonite wafer after being immersed in an aqueous composition containing 0.05 wt. % of surfactant GS12 for 5 minutes.
Figure 8B:
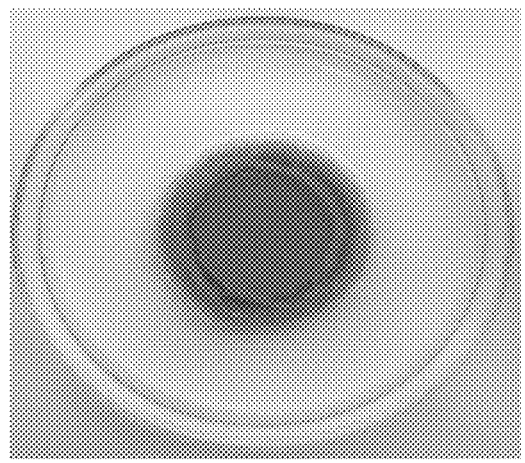
FIG. 8B is a picture of a bentonite wafer after being immersed in an aqueous composition containing 0.05 wt. % of surfactant GS12 for 5 hours.
Figure 8C:
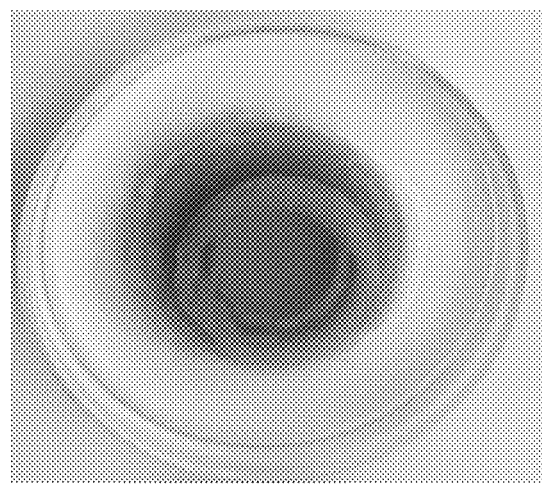
FIG. 8C is a picture of a bentonite wafer after being immersed in an aqueous composition containing 0.05 wt. % of surfactant GS12 for 24 hours.
Figure 9A:
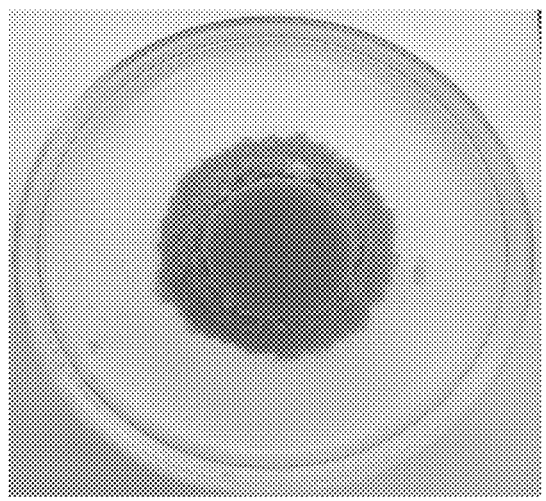
FIG. 9A is a picture of a bentonite wafer after being immersed in an aqueous solution containing 0.05 wt. % of surfactant GS12 and 3 wt. % of KCl for 5 minutes.
Figure 9B:
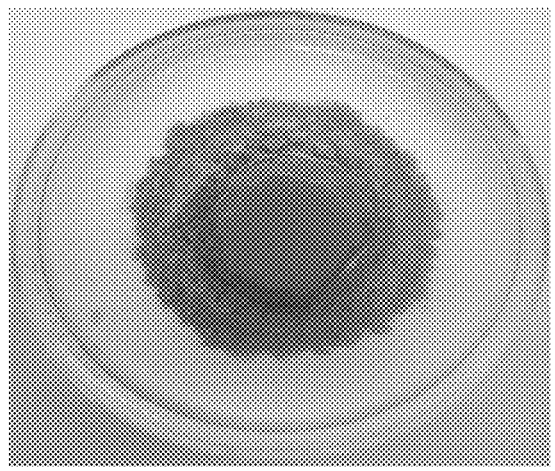
FIG. 9B is a picture of a bentonite wafer after being immersed in an aqueous solution containing 0.05 wt. % of surfactant GS12 and 3 wt. % of KCl for 5 hours.
Figure 9C:
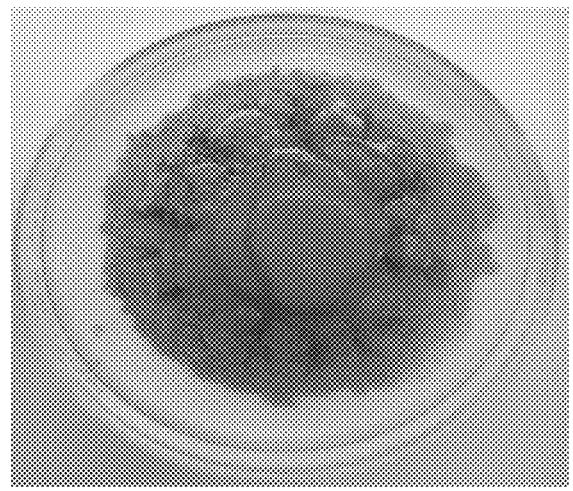
FIG. 9C is a picture of a bentonite wafer after being immersed in an aqueous solution containing 0.05 wt. % of surfactant GS12 and 3 wt. % of KCl for 24 hours.

FIGS. 3-5 show the clay swelling results using surfactants GS8, GS10, and GS12 with different spacer lengths, respectively. These tests were performed on solutions containing three different concentrations of each surfactant. The surfactant concentration resulted in the least clay swelling was determined to be the optimum concentration.

Initially, the clay swelling was reduced as surfactant concentration increased from 0.025% to 0.05% by weight relative to a total weight of the solution. However, further raises in the surfactant concentration to above 0.05 wt. % (e.g., 0.1 wt. %) did not lead to greater inhibition in clay swelling. Importantly, linear clay swelling results demonstrate that the addition of any surfactant disclosed herein significantly reduced the swelling of clay, compared to the degree of clay swelling caused by deionized water (DW).

It was also observed that the surfactant containing a longer carbon chain (GS12) was more effective in reducing the swelling than the surfactant with shorter carbon chains (GS8, GS10) (see Table 1).

TABLE 1

Linear swelling results of synthesized gemini surfactants

| Surfactant | Surfactant Concentration wt. % | Swelling % at 12 hours | Swelling % at 24 hours | Swelling % at 40 hours |
|---|---|---|---|---|
| Deionized Water | 0 | 84 | 125 | 171 |
| GS8 | 0.025 | 77 | 108 | 140 |
|  | 0.05 | 71 | 101 | 132 |
|  | 0.1 | 73 | 104 | 136 |
| GS10 | 0.05 | 76 | 109 | 140 |
|  | 0.1 | 78 | 112 | 145 |
| GS12 | 0.025 | 73 | 107 | 145 |
|  | 0.05 | 67 | 95 | 124 |
|  | 0.075 | 69.86 | 98.7 | 129.99 |
|  | 0.1 | 72 | 103 | 137 |

Example 7

Free Swelling Test: Comparison with Conventional Inhibitor (KCl)

Free swelling tests were also conducted by exposing bentonite wafers to different fluids in a glass plate. The free swelling of the clay was observed at different time intervals. In this experiment, bentonite wafer was placed in a glass plate and 80 mL of each swelling inhibitor was poured onto the glass plate. Then the free swelling test was performed at room temperature.

Free swelling test was performed on a surfactant solution containing 0.05 wt. % GS12 by weight concentration. Also, a mixture solution containing 3% by weight of KCl and 0.05% by weight GS12 surfactant was prepared and tested. To compare the swelling inhibition performance of surfactant to conventional inhibitor KCl, the swelling effect of a solution containing deionized water and 3% by weight KCl on bentonite wafers was also investigated.

Solutions containing potassium-based salts have been widely utilized as shale inhibitor. The performance of the currently disclosed surfactants was evaluated and compared to KCl. The photographs depicting swelling of bentonite wafers after exposing to deionized water, 3 wt. % KCl, 0.05 wt % of GS12, and a mixture of 0.05 wt. % GS12 and 3 wt. % KCl, respectively, were taken at different time intervals (5 min, 5 hours, and 24 hours) (see FIGS. 6A-C, 7A-C, 8A-C, and 9A-C).

When bentonite wafers were exposed to deionized (DI) water, they did not start to swell immediately upon exposure. It was observed that after 5 minutes' exposure, there was no change or deformation in shape observed. During this period, water was penetrating into the pores of bentonite. A similar trend was observed for surfactant solutions. Bentonite exposed to 0.05 wt. % GS12 solution behaved very similar to that exposed to DI water in the initial 5 minutes. Regarding 3% by weight KCl solution, the bentonite started to disintegrate immediately upon interaction with KCl solution. The rate of deformation was quite fast. For the mixture of 0.05 wt % GS12 surfactant and 3 wt % KCl, a similar pattern was observed with a bit slower disintegration rate.

The high rate of swelling of bentonite in water was noticed after prolonged exposure. There was clear swelling, and deformation occurred to bentonite after 24 hours of exposure. The 0.05 wt. % GS12 surfactant solution induced much smaller degrees of swelling and deformation to bentonite as compared to 3 wt. % KCl. The mixture of 3 wt. % KCl and 0.05 wt. % GS12 surfactant also resulted in the disintegration of the clay. This shows that the GS12 surfactant alone is more effective compared to KCl and KCl-surfactant solutions in clay swelling inhibition. KCl solutions may cause less clay swelling compared to water. However, as seen in the free swelling test, a complete disintegration of clay was observed using 3 wt % KCl solution. This is not acceptable for field applications as excessive clay disintegration may cause bit balling and cavings. Further, long term exposure to KCl salt can cause corrosion of drill strings and casings.

Example 8

Surfactants with a variety of spacers were synthesized and tested for their shale inhibition capacity using linear swelling and free swelling tests. All surfactants disclosed herein showed significantly superior clay swelling inhibition properties compared to deionized water according to the linear swelling test. In the free swelling tests, it was found that the surfactants did not disintegrate the clay and showed better clay swelling inhibition performance over KCl salt.

Based on the results, the presently disclosed surfactants exhibit great potential in reducing and/or inhibiting clay swelling that could help prevent formation damage and lower the operational cost.

The invention claimed is:

1. A method of stabilizing a subterranean geological formation containing a swellable clay, the method comprising:
treating the swellable clay with a composition comprising a surfactant of formula (I)

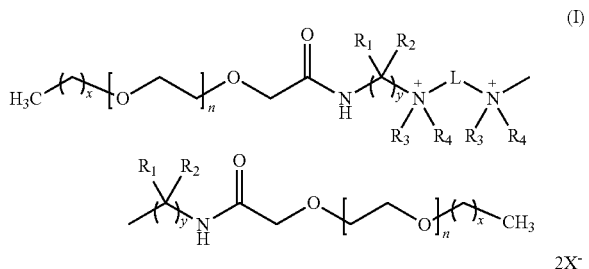

or a solvate thereof, a tautomer thereof, a stereoisomer thereof, or a mixture thereof;
wherein:
each of $R_1$ and $R_2$ are independently selected from the group consisting of a hydrogen, an optionally substituted alkyl, an optionally substituted cycloalkyl, and an optionally substituted arylalkyl;
each of $R_3$ and $R_4$ are independently selected from the group consisting of an optionally substituted alkyl, an optionally substituted cycloalkyl, and an optionally substituted arylalkyl;
L is —$(CH_2)_{12}$—;
each of n is independently an integer in a range of 1-15;
each of x is independently an integer in a range of 5-21;
each of y is independently an integer in a range of 2-5; and
X is an anion selected from the group consisting of a halide ion, a hexafluorophosphate ion, a trifluoromethanesulfonate ion, and a tetrafluoroborate ion.

2. The method of claim 1, wherein the swellable clay is at least one selected from the group consisting of a smectite clay, a kaolin clay, an illite clay, a chlorite clay, and a sepiolite clay.

3. The method of claim 1, wherein the swellable clay is a smectite clay.

4. The method of claim 3, wherein the smectite clay comprises montmorillonite.

5. The method of claim 1, wherein the composition further comprises an aqueous base fluid.

6. The method of claim 1, wherein the surfactant of formula (I) is present in an amount of 0.001-5 wt. % relative to a total weight of the composition.

7. The method of claim 1, wherein each of $R_1$ and $R_2$ are independently a hydrogen, or a methyl.

8. The method of claim 1, wherein each of $R_1$ and $R_2$ are a hydrogen.

9. The method of claim 1, wherein each of $R_3$ and $R_4$ are independently selected from the group consisting of a methyl, an ethyl, and an isopropyl.

10. The method of claim 1, wherein each of $R_3$ and $R_4$ are a methyl.

11. The method of claim 1, wherein each of n is an integer in a range of 2-11.

12. The method of claim 1, wherein each of x is an integer in a range of 11-13.

13. The method of claim 1, wherein each of y is 3.

14. The method of claim 1, wherein X is bromide.

15. A method of stabilizing a subterranean geological formation containing a swellable clay, the method comprising:
treating the swellable clay with a composition comprising a surfactant of formula (IV)

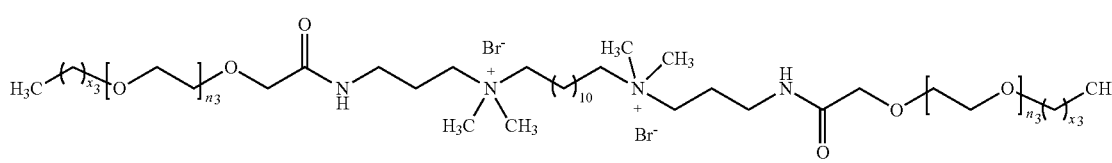

wherein:
each of $n_3$ is independently an integer in a range of 2-11; and
each of $x_3$ is independently an integer in a range of 11-13.

16. The method of claim 1, wherein the composition is substantially free of a potassium salt.

* * * * *